(12) United States Patent
Sauer

(10) Patent No.: US 12,070,190 B2
(45) Date of Patent: Aug. 27, 2024

(54) ENDOSCOPE GUIDE PORT

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 293 days.

(21) Appl. No.: 16/989,200

(22) Filed: Aug. 10, 2020

(65) Prior Publication Data

US 2021/0045619 A1 Feb. 18, 2021

Related U.S. Application Data

(60) Provisional application No. 62/886,752, filed on Aug. 14, 2019.

(51) Int. Cl.
*A61B 1/00* (2006.01)
*A61B 1/313* (2006.01)

(52) U.S. Cl.
CPC ........ *A61B 1/00154* (2013.01); *A61B 1/0016* (2013.01); *A61B 1/313* (2013.01)

(58) Field of Classification Search
CPC .... A61B 1/00154; A61B 1/0016; A61B 1/313
See application file for complete search history.

(56) References Cited

U.S. PATENT DOCUMENTS

| | | | | |
|---|---|---|---|---|
| 2,873,742 A | * | 2/1959 | Charles | A61M 16/0472 128/207.29 |
| 3,835,854 A | * | 9/1974 | Jewett | A61M 25/0113 604/159 |
| 5,389,100 A | * | 2/1995 | Bacich | A61M 25/0119 606/108 |
| 6,290,675 B1 | * | 9/2001 | Vujanic | A61M 25/0113 604/164.13 |
| 2003/0208187 A1 | | 11/2003 | Layer | |

OTHER PUBLICATIONS

International Search Report and Written Opinion mailed Nov. 16, 2021, for International Application No. PCT/US21/44675, filed Aug. 5, 2021.

* cited by examiner

*Primary Examiner* — Ryan N Henderson
*Assistant Examiner* — Megan Elizabeth Monahan
(74) *Attorney, Agent, or Firm* — Michael E. Coyne

(57) ABSTRACT

An endoscope port having a housing is disclosed. The housing of the endoscope port may include a channel passing therethrough, and a hub which may include a first roller and a second roller. The endoscope port may further include an entrance at an end of the channel, and an exit at an opposite end of the channel. The endoscope port may be configured such that when an actuator moves in a first rotational direction, a first roller moves in a second rotational direction, and a second roller moves in the first rotational direction.

6 Claims, 5 Drawing Sheets

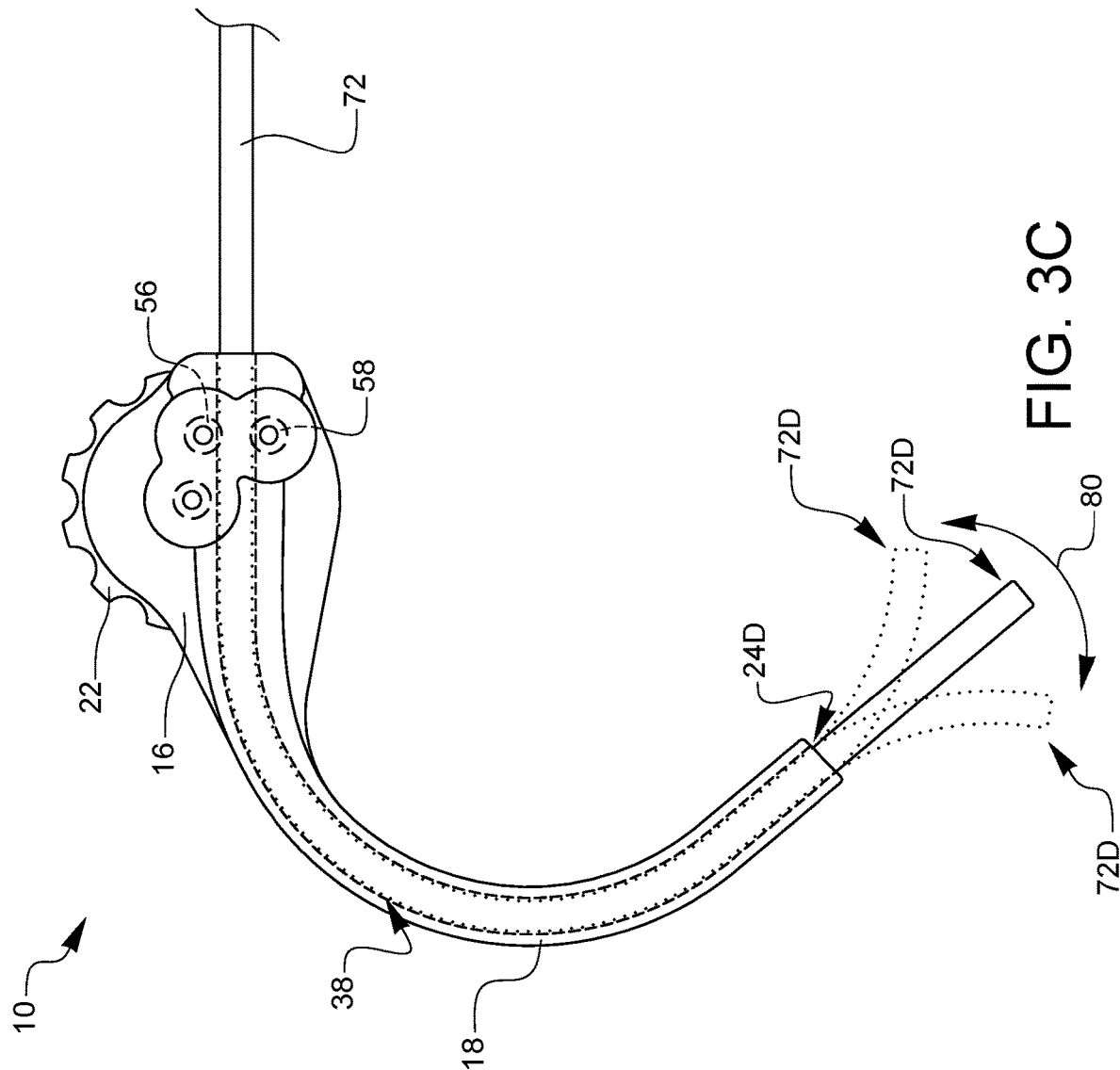

ENDOSCOPE GUIDE PORT

REFERENCE TO RELATED APPLICATIONS

This patent application claims priority to U.S. Provisional Patent Application No. 62/886,752 filed Aug. 14, 2019 and is entitled "ENDOSCOPE GUIDE PORT." The entire 62/886,752 application is hereby incorporated by reference in their entirety.

FIELD

The claimed invention relates to minimally invasive surgical devices, and more specifically to a surgical device used in guiding visualization during a minimally invasive surgical procedure.

BACKGROUND

Minimally invasive surgical approaches have gained increased interest in relation to many surgical procedures, including coronary surgical procedures. When a minimally invasive sub-xiphoid surgical approach is utilized, several surgical implement and tools, including visualization devices such as endoscopes are necessary to insure positive results and patient outcome. In instances where multiple tools are required, the area around the patient, and in particular, the surgical site may have limited space for additional visualization aids, for example, an endoscope.

While surgical equipment holders and endoscope delivery devices are employed by surgeons in this situation, most of them require mounting or introduction in such a way that may limit space needed for other necessary surgical implements, or for surgical staff to effectively perform the procedure. The placement of endoscopes or other visualization instrumentation is sometimes arranged or introduced in such a way that results in limiting the space available for other necessary tools and for surgical staff. Therefore, there is a need for suitable visualization management during minimally invasive surgical procedures that permit surgical staff visualization without obscuring motion or field of view.

BRIEF DESCRIPTION OF THE DRAWINGS

FIGS. 3A-3C are side partial cross-sectional views of the endoscope guide port of FIG. 1, illustrating the operational principles of the endoscope guide port.

Figure 1:
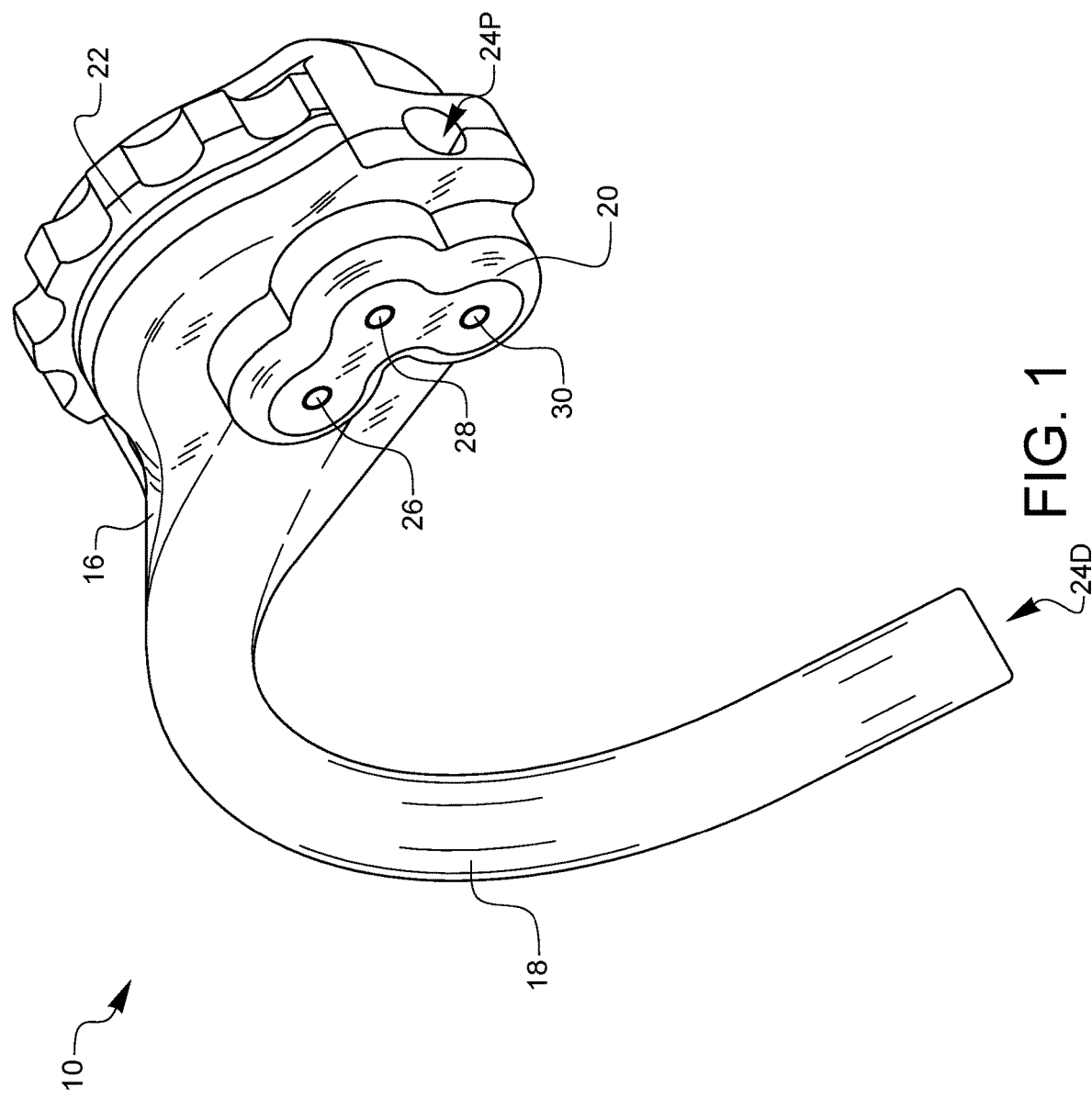
FIG. 1 is a top-left-front perspective view of one embodiment of an endoscope guide port.

It will be appreciated that for purposes of clarity and where deemed appropriate, reference numerals have been repeated in the figures to indicate corresponding features, and that the various elements in the drawings have not necessarily been drawn to scale in order to better show the features.

SUMMARY

An endoscope port having a housing is disclosed. The housing of the endoscope port may include a channel passing therethrough, and a hub which may include a first roller and a second roller. The endoscope port may further include an entrance at an end of the channel, and an exit at an opposite end of the channel.

The endoscope port is configured such that when an actuator moves in a first rotational direction, a first roller moves in a second rotational direction, and a second roller moves in the first rotational direction.

Another endoscope port is disclosed. The endoscope port may also include a housing which includes an arcuate channel passing therethrough, an actuator movably coupled to the housing, an actuator roller coupled to the actuator, an actuator gear coupled to the actuator roller, a first roller gear movably coupled to the actuator gear, a first roller coupled to the first roller gear, a second roller gear movably coupled to the first roller gear, and a second roller coupled to the second roller gear.

DETAILED DESCRIPTION

FIG. 1 is a top-left-front perspective view of one embodiment of an endoscope guide port. An endoscope guidance port 10 is illustrated in FIG. 1, the endoscope port 10 comprised of a housing 16 defining a gear hub 20, and a disc-shaped dial actuator 22 coupled to the housing 16 The housing 16 defines an arcuate channel, not visible in this view, passing therethrough. The channel 24 has a proximal port opening 24P and a distal port opening 24D at the opposite end of a neck 18 also defined by the housing 16 of the endoscope guidance port 10 and is configured to guide an endoscope from the entrance of the channel towards the exit of the channel. Several axles 26, 28, 30 are rotatably coupled to the gear hub 20 on the housing 16 of the endoscope guidance port 10.

Figure 2:
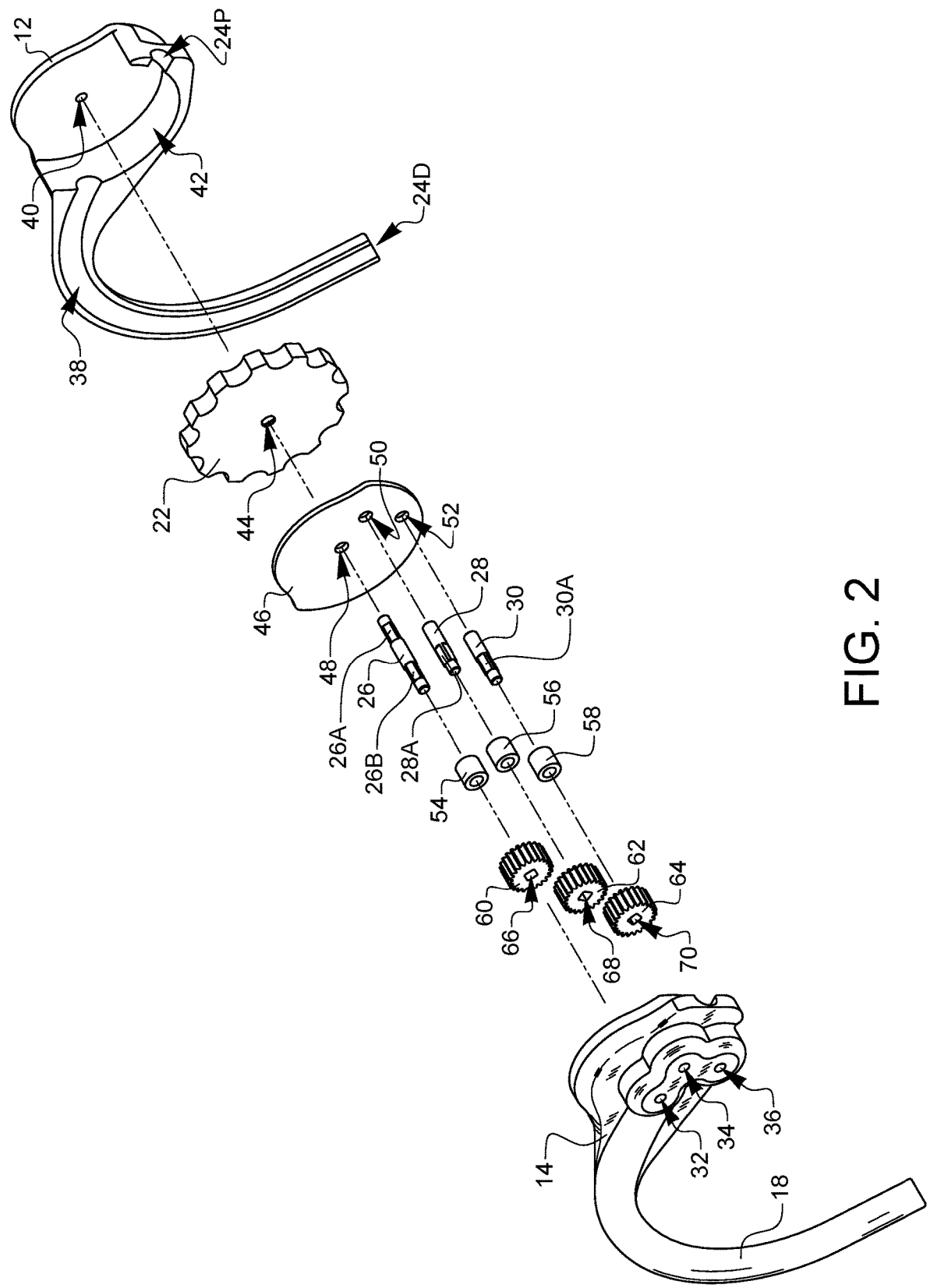
FIG. 2 is an exploded view illustrating the assembly steps of the endoscope guide port of FIG. 1.

FIG. 2 is an exploded view illustrating the assembly steps of the endoscope guide port of FIG. 1. The first housing half 12 defines part of a port channel 24, a portion of the proximal port opening 24P, a portion of distal port opening 24D, a housing recess 42, and a hole 40. The hole 40 is aligned with a keyed hole 44 defined by the dial actuator 22. The dial actuator 22 is inserted and held within the housing recess 42 on the first housing half 12. Next, a bearing plate 46 is stacked against the dial actuator 22, the bearing plate 46 defining a center hole 48 aligned with keyed hole 44 in the dial actuator 22 and the mounting hole 40 in the first housing half 12. The bearing plate 46 also defines a hole 50 and another hole 52 configured to accept axle 28 and axle 30 respectively. Axle 26 defines two keyed portions 26A, 26B and is configured to be inserted into hole 48 in the bearing plate 46, hole 44 in dial actuator 22, and hole 40 in the first housing half 12. Keyed portion 26A fits into keyed hole 44 in dial actuator 22. A spacer or actuator roller 54 is placed over axle 26 followed by dial actuator gear 60, which also has a keyed hole 66, configured to interface with keyed portion 26B on axle 26. Axle 28 defines a single keyed portion 28a and is inserted into hole 50 in bearing plate 46. A first upper roller guide 56 is placed over axle 28 followed by a first upper roller gear 62, which defines a keyed hole 68, configured to interface with keyed portion 28a on axle 28. Axle 30 defines a single keyed portion 30a and is inserted into hole 52 in bearing plate 46. A second lower roller guide 58 is placed over axle 30 followed by a second lower roller gear 64, which defines a keyed hole 70, configured to interface with keyed portion 30A on axle 30. The dial actuator 22 and the described set of axles 26, 28, 30, rollers 54, 56, 58, and gears 60, 62, 64 are configured to interact, enmesh, and turn such that they guide an endoscope from the proximal port opening 24P through port channel 24 and out of distal port opening 24D. Finally, the second housing half 14 is placed onto the first housing half 12 completing the assembly. The second housing half 14 defines several holes 32, 34, 36 which capture the ends of axles 26, 28, 30 respectively. Features in the second housing half 14 not visible in this view also complement and complete corresponding features, for example, the port channel 24, the proximal port opening 24P, and the distal port opening 24D, in the first housing half 12. The first housing half 12 and second housing half 14 are fixedly attached via welding, adhesion, or other means known to those skilled in the arts. This embodiment of an endoscope guidance port is shown having an arcuate-shaped neck and channel, the arc of the curvature of the neck and channel in other embodiments may have other arcuate shapes than the one described and depicted herein. Alternatively, other embodiments may have articulatable segments or an adjustable curvature built into the housing. While rollers and axles and gears are shown in this embodiment as the structure and mechanism for advancing an endoscope or other visualization means into a surgical location, other mechanical means may be used such as a rack and pinion, gears, motors, or combinations thereof.

Figure 3A:
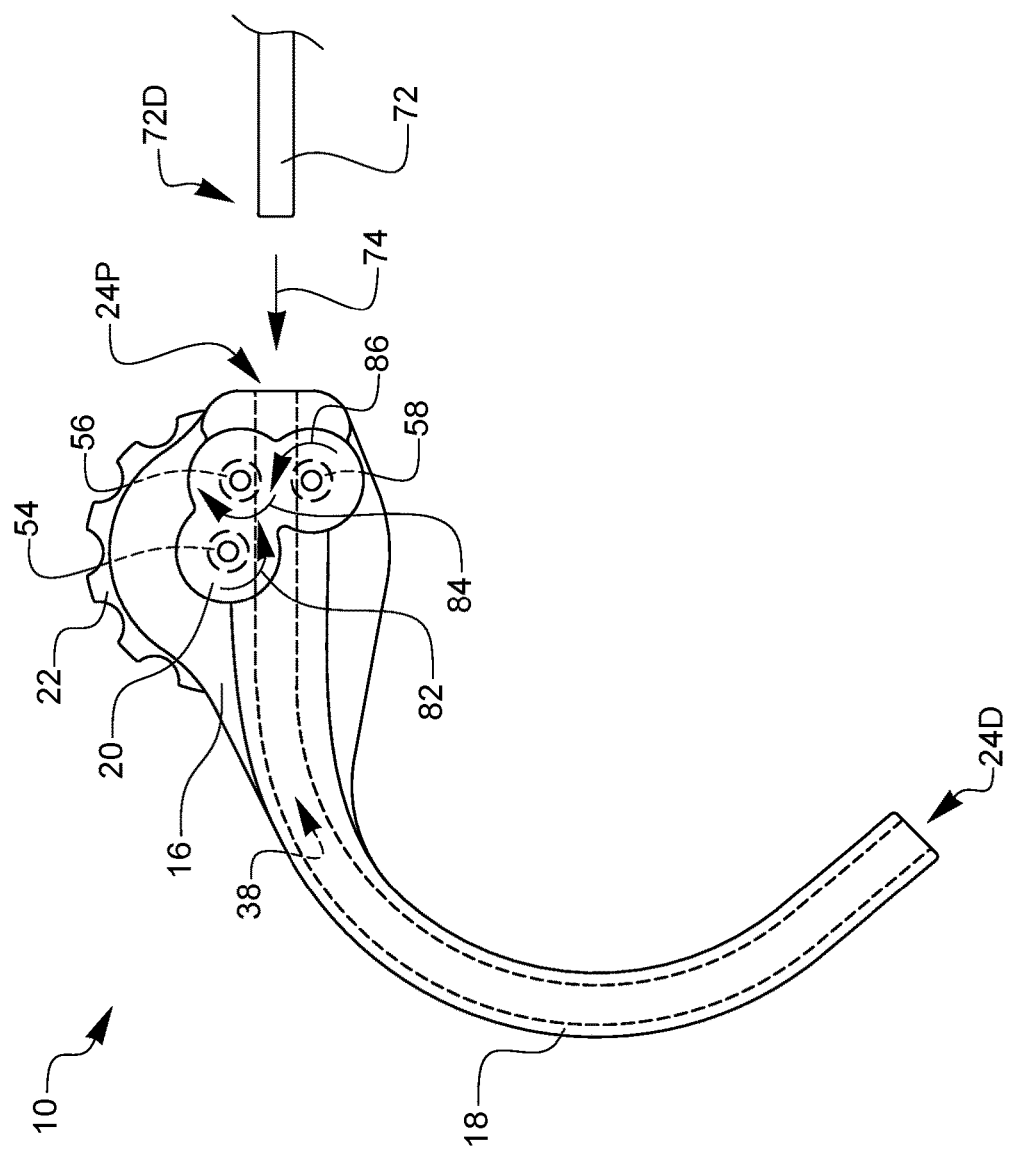
Figure 3B:
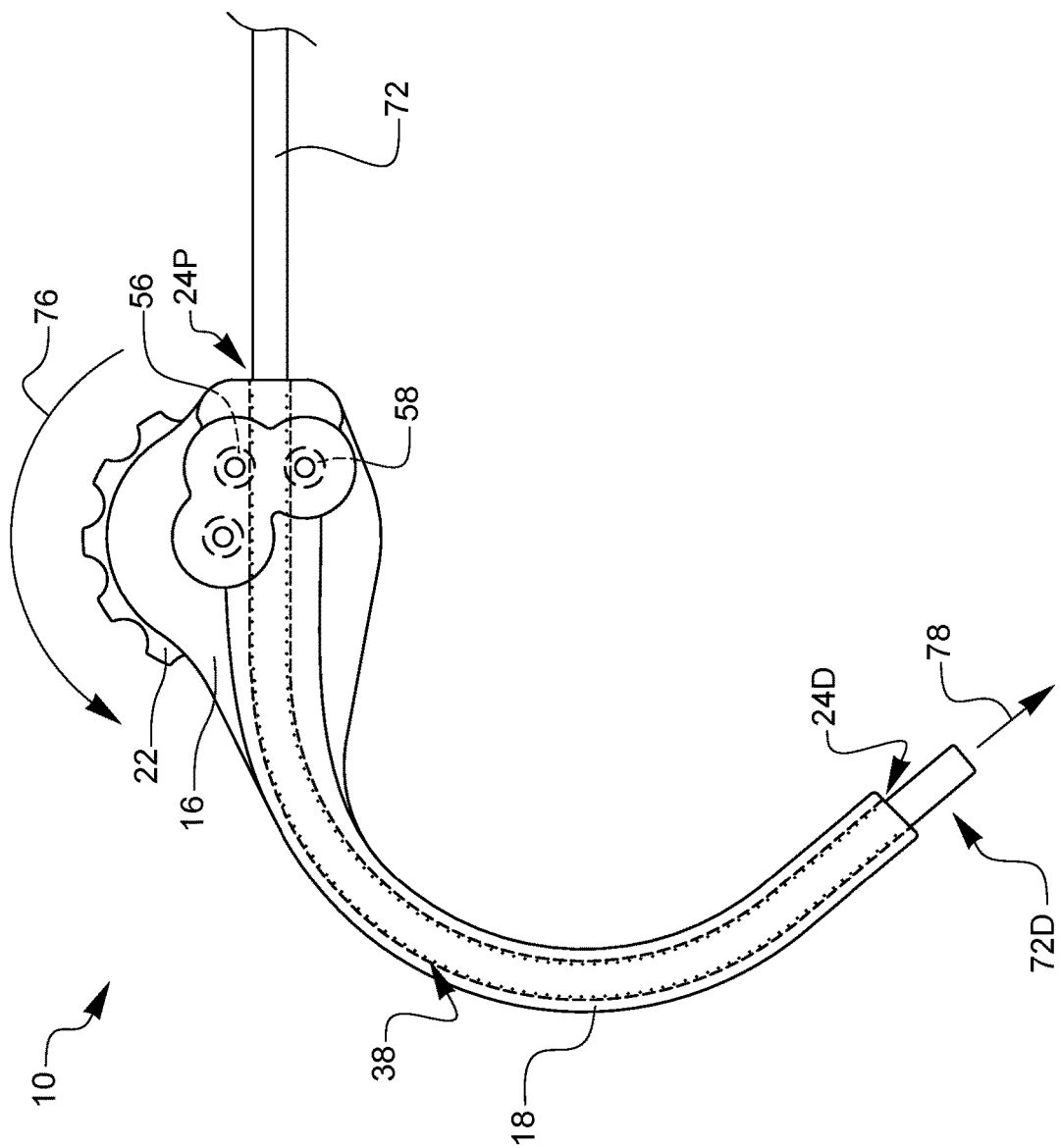

FIGS. 3A-3C are side partial cross-sectional views of the endoscope guide port of FIG. 1, illustrating the operational principles of the endoscope guide port. FIG. 3A illustrates the insertion of an endoscope 72 by placing the distal end 72D into the proximal port opening 24P in direction 74. Manual insertion of the endoscope 72 until it contacts and is held between first upper roller guide 56 and second lower roller guide 58 is shown.

FIG. 3B illustrates the endoscope 72 fully inserted into the endoscope guidance port 10, having passed substantially through the port channel 24. The distal end 72D of the endoscope 72 is shown exiting the distal port opening 24D of the endoscope guidance port 10 further in direction 78. This is achieved by rotating dial 22 in direction 76, which turns actuator gear 60 in direction 82, gear 62 and therefore first upper roller guide 56 in direction 84, and also gear 64 and therefore second lower roller guide 58 in direction 86. The first upper roller guide 56 and second lower roller guide 58 contact and push the endoscope 72 in direction 78, eventually advancing the endoscope 72 such that it exits the port channel 24 and emerges from distal port opening 24D of the endoscope guidance port 10. Thus, when the dial actuator 22 moves in a first rotational direction 76, the first roller 56 moves in a second rotational direction 84, and the second roller moves in the first rotational direction 86, which is the same as direction 76.

FIG. 3C illustrates the endoscope 72 with its distal end 72D exited from the distal port opening 24D of the endoscope guidance port 10. The endoscope can now be controlled to move in direction 80. The endoscope can be controlled and moved in direction 80 or in a direction in multiple other planes with respect to the distal port opening 24D. Also, the distal end 72D of the endoscope 72 may be articulated or controlled by any number of means known to those skilled in the arts, such as, but not limited to connecting rods, mechanical cables, fluidic actuation systems, pulley systems, shape memory alloys, or combinations thereof.

This embodiment of an endoscope guidance port is shown having an arcuate shaped channel that allows an endoscope to be mounted or introduced in a location towards a patient's head, or from a cephalad direction, and aim the visualization area of the endoscope towards a similar cephalad direction once introduced into a surgical site from a sub-xiphoid incision site location. Given the curved, arcuate nature of the endoscope guidance port described herein, the device as shown could also be used as a retractor, used to lift the ribcage or other anatomical features up or in a direction such that additional room is provided in the patient for the surgical procedure. Utilizing an endoscope guidance port such as the one described herein, or in similar embodiments, allows for increased space in and around the surgical site, resulting in the direct visualization of minimally invasive surgical procedures without compromising maneuverability of the surgeon or crowding the placement or location of other surgical tools or devices used in a minimally invasive surgical procedure.

Various advantages of an endoscope guide port have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A guide port configured to guide a surgical instrument, comprising:
a housing having one or more interior surfaces that define an interior portion, the housing having an aperture formed in an external surface that opens to the interior portion;
a neck coupled to the housing, the neck extending along a neck axis from a proximal end of the neck to a distal end of the neck, wherein a passage extends through the neck from the proximal end of the passage to the distal end of the passage, wherein the proximal end of the passage is open to the interior portion of the housing, wherein the neck axis has an arcuate shape when viewed normal to the neck axis, the neck axis extending from the proximal end of the neck to the distal end of the neck and the housing and neck are integrally formed as a unitary part, and
a channel extending from a proximal end of the channel to a distal end of the channel, wherein the channel extends from the distal end of the passage to the proximal end of the passage, through a portion of the interior portion of the housing, and to the aperture formed in the housing such that the proximal end of the channel is disposed at or adjacent to the aperture formed in the housing and such that the distal end of the channel is disposed at the distal end of the passage through the neck, and wherein the channel is configured to receive the surgical instrument;
a dial actuator rotatably coupled to the housing, wherein the dial actuator has a shape of a disc having a center aperture, wherein the dial actuator rotates about a first portion of a dial actuator axle such that the first portion of the dial actuator axle extends through the center aperture of the disc, wherein a first portion of the disc defining the center aperture is disposed within the interior portion of the housing and a second portion of the disc disposed along a portion of a perimeter edge of the disc is disposed through a slot opening formed in the housing such that the second portion of the disc is disposed external to the housing;

a dial actuator gear rotatably coupled to the housing, wherein the dial actuator gear rotates about a second portion of the dial actuator axle such that when the dial actuator rotates about the dial actuator axle in a first rotational direction, the dial actuator gear also rotates about the dial actuator axle in the first rotational direction;

a first upper roller gear rotatably coupled to the housing, wherein the first upper roller gear rotates about a first portion of a first upper roller axle, and wherein the first upper roller gear engages the dial actuator gear such that when the dial actuator gear rotates about the dial actuator axle in the first rotational direction, the first upper roller gear rotates about the first portion of the first upper roller axle in a second rotational direction;

a first upper roller guide disposed on a second portion of the first upper roller axle, wherein when the first upper roller gear rotates about the first portion of the first upper roller axle in the second rotational direction, the first upper roller guide rotates about the second portion of the first upper roller axle in the second rotational direction, wherein a portion of the first upper roller guide is adjacent to a first portion of the channel such that the portion of the first upper roller guide contacts a first portion of the surgical instrument when the surgical instrument is received in the channel;

a second lower roller gear rotatably coupled to the housing, wherein the second lower roller gear rotates about a first portion of a second lower roller axle, and wherein the second lower roller gear engages the first upper roller gear such that when the first upper roller gear rotates about the first upper roller axle in the second rotational direction, the second lower roller gear rotates about the first portion of the second lower roller axle in the first rotational direction; and a second lower roller guide disposed on a second portion of the second lower roller axle, wherein when the second lower roller gear rotates about the first portion of the second lower roller axle in the first rotational direction, the second lower roller guide rotates about the second portion of the second lower roller axle in the first rotational direction, wherein a portion of the second lower roller guide is adjacent to a second portion of the channel such that the portion of the second lower roller guide contacts a second portion of the surgical instrument when the surgical instrument is received in the channel, wherein when the dial actuator is rotated in the first rotational direction, the portion of the first upper roller guide rotating in the second rotational direction and the portion of the second lower roller guide rotating in the first rotational direction cooperate to displace the surgical instrument in a first linear direction towards the distal end of the channel, and wherein the dial actuator gear rotates in a first plane, the first upper roller gear rotates in the first plane, and the second lower roller gear rotates in the first plane.

2. The guide port of claim 1, wherein when the dial actuator is rotated in the second rotational direction, the first upper roller guide rotates in the first rotational direction and the second lower roller guide rotates in the second rotational direction, and the portion of the first upper roller guide rotating in the first rotational direction and the portion of the second lower roller guide rotating in the second rotational direction cooperate to displace the surgical instrument in a second linear direction towards the proximal end of the channel.

3. The guide port of claim 1, further comprising:
an actuator roller disposed on a third portion of the dial actuator axle and configured to rotate about the third portion of the dial actuator axle in the first rotational direction when the dial actuator is rotated in the first rotational direction, wherein a portion of the actuator roller is adjacent to a third portion of the channel such that the portion of the actuator roller contacts a third portion of the surgical instrument when the surgical instrument is received in the channel.

4. The guide port of claim 3, wherein the third portion of the dial actuator axle is between the first portion of the dial actuator axle and the second portion of the dial actuator axle.

5. The guide port of claim 1, wherein the neck is rigid.

6. The guide port of claim 1, wherein a portion of the dial actuator gear is in contact with a first portion of the first upper roller gear such that the first upper roller gear directly engages the dial actuator gear, and wherein a second portion of the first upper roller gear is in contact with a portion of the second lower roller gear such that the first upper roller gear directly engages the second lower roller gear.

* * * * *